United States Patent
Chiang et al.

(10) Patent No.: US 10,741,036 B1
(45) Date of Patent: Aug. 11, 2020

(54) SMOKE DETECTOR FOR FALSE ALARM REDUCTION

(71) Applicant: Sercomm Corporation, Taipei (TW)

(72) Inventors: Meng-Chien Chiang, Taipei (TW); Cheng-Jeng Chou, Taipei (TW)

(73) Assignee: Sercomm Corporation, Taipei (TW)

( * ) Notice: Subject to any disclaimer, the term of this patent is extended or adjusted under 35 U.S.C. 154(b) by 0 days.

(21) Appl. No.: 16/548,807

(22) Filed: Aug. 22, 2019

(30) Foreign Application Priority Data

Jan. 31, 2019 (CN) .......................... 2019 1 0101039

(51) Int. Cl.
  *G08B 17/00* (2006.01)
  *G08B 17/107* (2006.01)
  *G01N 21/3504* (2014.01)
  *G08B 17/117* (2006.01)
  *G01N 33/00* (2006.01)

(52) U.S. Cl.
  CPC ....... *G08B 17/107* (2013.01); *G01N 21/3504* (2013.01); *G01N 33/004* (2013.01); *G01N 33/0063* (2013.01); *G08B 17/117* (2013.01)

(58) Field of Classification Search
  CPC .............. G08B 17/107; G08B 17/117; G01N 21/3504; G01N 33/004; G01N 33/0063
  USPC ................................................. 340/628–632
  See application file for complete search history.

(56) References Cited

U.S. PATENT DOCUMENTS

| | | | | |
|---|---|---|---|---|
| 8,907,802 B2* | 12/2014 | Erdtmann | ............ | G08B 17/107 250/573 |
| 2011/0121654 A1* | 5/2011 | Recker | .................. | H02J 7/0068 307/66 |
| 2011/0175741 A1* | 7/2011 | Slemon | ................ | G08B 17/107 340/630 |
| 2011/0260876 A1* | 10/2011 | Riedi | .................... | G08B 17/107 340/630 |
| 2012/0126700 A1* | 5/2012 | Mayfield | ................ | G08B 7/062 315/86 |
| 2012/0199744 A1* | 8/2012 | Martin | ................. | G01N 21/031 250/343 |
| 2013/0229658 A1* | 9/2013 | Jouanique-Dubuis | ....................... | G01J 3/0289 356/437 |

(Continued)

FOREIGN PATENT DOCUMENTS

| CN | 1418358 A | 5/2003 |
|---|---|---|
| CN | 1489756 A | 4/2004 |

(Continued)

*Primary Examiner* — Ojiako K Nwugo
(74) *Attorney, Agent, or Firm* — Winston Hsu

(57) ABSTRACT

A smoke detector comprising: a first light source, configured to generate first light beam; a second light source, configured to generate second light beam; a light receiver, configured to respectively generate a first and a second original light detecting signal in response to the first light beam and the second light beam, wherein an energy conversion efficiency of the light receiver at the first wavelength is different from an energy conversion efficiency of the light receiver at the second wavelength; a signal adjusting circuit, configured to amplify the second original light detecting signal to generate a second light detecting signal; and a driving and determining circuit, configured to determine signal intensities of the first original light detecting signal and the second light detecting signal.

9 Claims, 5 Drawing Sheets

(56) References Cited

U.S. PATENT DOCUMENTS

| | | | | |
|---|---|---|---|---|
| 2014/0009295 A1* | 1/2014 | Kim | ............... | G08B 21/18 340/632 |
| 2014/0015668 A1* | 1/2014 | Hanses | ............... | G08B 17/107 340/514 |
| 2014/0015681 A1* | 1/2014 | Engelmann | ............ | G08B 17/103 340/630 |
| 2014/0197957 A1* | 7/2014 | Fischer | ............... | G08B 17/107 340/630 |
| 2014/0333928 A1* | 11/2014 | Erdtmann | ............ | G08B 17/107 356/338 |
| 2015/0042991 A1* | 2/2015 | Hankiewicz | ............ | G01N 21/39 356/326 |
| 2015/0228171 A1* | 8/2015 | Aebersold | ............ | G08B 17/107 340/630 |
| 2017/0138879 A1* | 5/2017 | Akiyama | ............ | G01N 27/129 |
| 2017/0241931 A1* | 8/2017 | Kitazawa | ............... | G01N 27/12 |

FOREIGN PATENT DOCUMENTS

| | | |
|---|---|---|
| CN | 101952863 A | 1/2011 |
| CN | 103026393 A | 4/2013 |
| WO | 2016206000 A1 | 12/2016 |

* cited by examiner

SMOKE DETECTOR FOR FALSE ALARM REDUCTION

CROSS REFERENCE TO RELATED APPLICATION

This application claims priority to China Patent Application No. 201910101039.5, filed on 2019 Jan. 31. The contents thereof are incorporated herein by reference.

BACKGROUND OF THE INVENTION

1. Field of the Invention

The present invention relates to a smoke detector, and particularly relates to a smoke detector uses light of different spectrums to reduce false alarms.

2. Description of the Prior Art

Smoke detectors are widely used in different places to detect smoke, thereby alarms can be generated to inform users when a fire breaks out. By this way, the damage caused by the fire can be minimized. However, a conventional smoke detector cannot easily distinguish between different types of smoke, thus a false alarm may be made. For example, cooking and cigarette smoking may be erroneously detected as fire and trigger a false alarm. Such error may cause panic to or perplex users.

SUMMARY OF THE INVENTION

One objective of the present invention is to provide a smoke detector for reducing false alarms. One embodiment of the present invention discloses a smoke detector, which comprises: a first light source, configured to generate first light beam with a first wavelength; a second light source, configured to generate second light beam with a second wavelength; a light receiver, configured to generate a first original light detecting signal in response to first scattered light of the first light beam, and configured to generate a second original light detecting signal in response to second scattered light of the second light beam, wherein a first energy conversion efficiency of the light receiver at the first wavelength is different from a second energy conversion efficiency of the light receiver at the second wavelength; a signal adjusting circuit, configured to amplify the second original light detecting signal to generate a second light detecting signal; and a driving and determining circuit, coupled to the first light source, the second light source, the light receiver, and the signal adjusting circuit, configured to determine signal intensities of the first original light detecting signal and the second light detecting signal.

Another embodiment of the present invention discloses a smoke detecting method, which comprises: generating first light beam by a first light source, and generating a first original light detecting signal in response to first scattered light of the first light beam by a light receiver, wherein the first light beam has a first wavelength; controlling the first light source to cease generating the first light beam, generating second light beam by a second light source and generating a second original light detecting signal in response to second scattered light of the second light beam by the light receiver, if a signal intensity of the first light detecting signal is larger than or equal to a first signal threshold value, wherein the second light beam has a second wavelength; amplifying the second original light detecting signal to generate a second light detecting signal; and generating a warning message if a signal intensity of the second light detecting signal is not larger than a second signal threshold value.

In view of above-mentioned embodiments, two stages or more stages smoke detecting method can be applied to determine whether a fire breaks out or not, thus false alarms can be reduced. Additionally, the present invention can use a single light receiver to receive light of different spectrums, thus the circuit or device size and cost can be reduced because no need to use two separated receiver for specific spectrums.

These and other objectives of the present invention will no doubt become obvious to those of ordinary skill in the art after reading the following detailed description of the preferred embodiment that is illustrated in the various figures and drawings.

DETAILED DESCRIPTION

In following descriptions, several embodiments are provided to explain the concept of the present invention. Components in each embodiment can be implemented by hardware (e.g. a circuit or a device), or implemented by firmware (e.g. a processor installed a corresponding program). Additionally, the terms "first", "second" . . . are only for defining different components or steps, but do not mean to limit sequences thereof. Furthermore, components in each embodiment can be integrated to fewer components or divided into more components.

Figure 1:
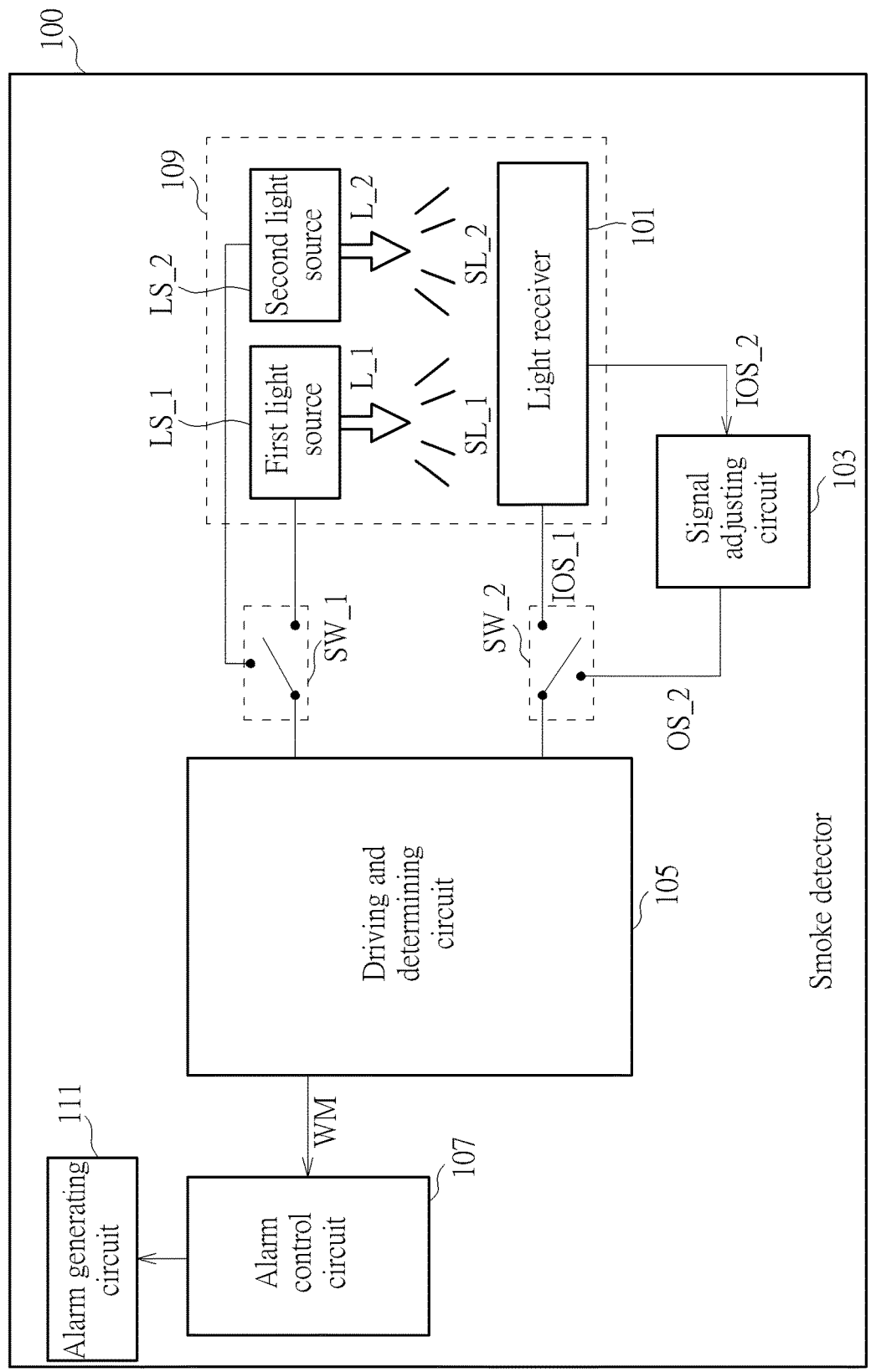
FIG. 1 is a circuit block diagram illustrating a smoke detector according to one embodiment of the present invention.

FIG. 1 is a circuit block diagram illustrating a smoke detector 100 according to one embodiment of the present invention. As illustrated in FIG. 1, the smoke detector 100 comprises a first light source LS_1, a second light source LS_2, a light receiver 101, a signal adjusting circuit 103, a driving and determining circuit 105, and an alarm control circuit 107. The first light source LS_1 is configured to generate first light beam L_1 with a first wavelength. The second light source LS_2 is configured to generate second light beam L_2 with a second wavelength. The light receiver 101 can generate a first original light detecting signal IOS_1 in response to first scattered light SL_1 of the first light beam L_1, and can generate a second original light detecting signal IOS_2 in response to second scattered light SL_2 of the second light beam L_2. A first energy conversion efficiency of the light receiver 101 at the first wavelength is different from a second energy conversion efficiency of the light receiver 101 at the second wavelength. That is, the light receiver 101 transforms light to currents while receiving the first scattered light SL_1 and the second scattered light SL_2, to generate corresponding light detecting signals. However, the generated first original light detecting signal IOS_1 and the second original light detecting signal IOS_2 have different signal intensities even if the light receiver 101 receives the first scattered light SL_1 and the second scattered light SL_2 with the same light intensities. In other words, the light receiver 101 has different responses for the first wavelength and for the second wavelength. The light receiver 101 can be implemented by an optical to electrical converting circuit, which can generate currents in response to light.

The first wavelength is the wavelength with the highest intensity in the first light beam's spectrum. The second wavelength is the wavelength with the highest intensity in the second light beam's spectrum.

In one embodiment, the first light source LS_1, the second light source LS_2 and the light receiver 101 are provided in a smoke chamber 109. If no smoke is in the smoke chamber 109, the light receiver 101 receives none of (or only a trivial of) the first light beam L_1, the second light beam L_2, the first scattered light SL_1 or the second scattered light SL_2, thus values of the first original light detecting signal IOS_1 and the second original light detecting signal IOS_2 can be zero or approach zero. The smoke chamber 109 can receive external air, thus smoke will enter the smoke chamber 109 if the air contains smoke. First scattered light SL_1 and second scattered light are respectively generated when the first light beam L_1 and the second light beam L_2 are scattered by smoke particles in the smoke. The signal adjusting circuit 103 is configured to amplify the second original light detecting signal IOS_2 to generate a second light detecting signal OS_2, to compensate for the difference between the first light source LS_1 and the second light source LS_2 and the different responses of the light receiver 101 for the first wavelength and the second wavelength. By this way, the difference between the signal intensity of the second light detecting signal OS_2 and the first original light detecting signal IOS_1 can fall in a predetermined range.

The driving and determining circuit 105 is coupled to the first light source LS_1, the second light source LS_2 and the light receiver 101. At the beginning, the switch SW 1 makes the driving and determining circuit 105 couple to the first light source LS_1, and the switch SW 2 makes the light receiver 101 couple to the driving and determining circuit 105 but makes the signal adjusting circuit 103 not couple to the driving and determining circuit 105. The driving and determining circuit 105 drives the first light source LS_1 to generate the first light beam L_1. In such case, if a signal intensity of the first original light detecting signal IOS_1 is larger than or equal to a first signal threshold value, the detected smoke may be caused by a fire. After that, the switch SW 1 makes the driving and determining circuit 105 couple to the second light source LS_2, and the switch SW 2 makes the signal adjusting circuit 103 couple to the driving and determining circuit 105. The driving and determining circuit 105 drives the second light source LS_2 to generate the second light beam L_2 and controls the first light source LS_1 not to generate light. In such case, if a signal intensity of the second light detecting signal OS_2 is not larger than a second signal threshold value, it means the detected smoke is really caused by a fire, thus a warning message WM is generated. On the opposite, if the signal intensity of the second light detecting signal OS_2 is greater than the second signal threshold value, it means the detected smoke is not caused by a fire, but likely by cooking, thus no warning message WM is generated.

Please note, the smoke detector 100 is not limited to comprise the switch SW 1 or the switch SW 2. For example, the driving and determining circuit 105 can directly connect to the first light source LS_1 and the second light source LS_2, and controls which one of the first light source LS_1 and the second light source LS_2 emits light via adjusting the currents provided to the light source LS_1 and the second light source LS_2. Similarly, the driving and determining circuit 105 can directly connect to the light receiver 101 and the signal adjusting circuit 103, and can select whether signal provided by the former or the latter should be used.

In one embodiment, the detecting threshold values which the driving and determining circuit 105 use for the first original light detecting signal IOS_1 and the second light detecting signal OS_2 are the same by amplifying the second light detecting signal. In other words, the above-mentioned first signal threshold value and the second signal threshold value are the same by using the trick to amplify the second light detecting signal. After the alarm control circuit 107 receives the warning message WM, the alarm control circuit 107 controls the alarm generating circuit 111 to generate alarms. The alarm can be any kind of message, such as sound, light, vibration, images, or any other message that can be transmitted to other electronic devices. The alarm control circuit 107 and the alarm generating circuit 111 can be integrated to a single component.

As above-mentioned, the signal adjusting circuit 103 can amplify the second original light detecting signal IOS_2. By this way, the smoke detector 100 can use only one light receiver and the same calibration values to receive light of two different spectrums for the two stages smoke determination, thus the circuit size and cost can be reduced. This is the biggest benefit. The above-mentioned calibration values are referential values which the driving and determining circuit 105 uses to compensate for factors such as aging of components and variation of caused by manufacturing or environment.

Figure 2:
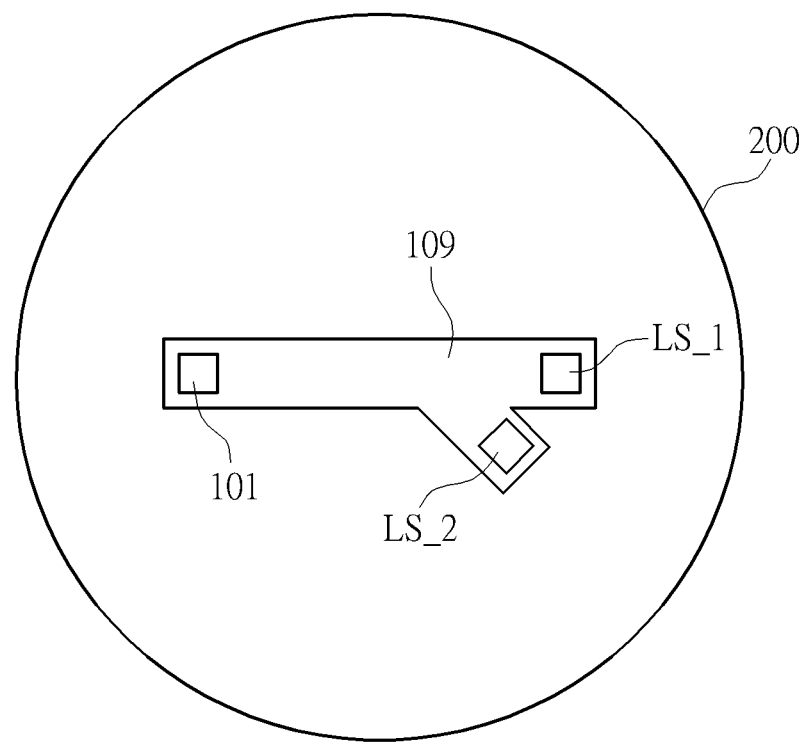
FIG. 2 and FIG. 3 are schematic diagrams illustrating structures of a smoke detector according to embodiments of the present invention.
Figure 3:
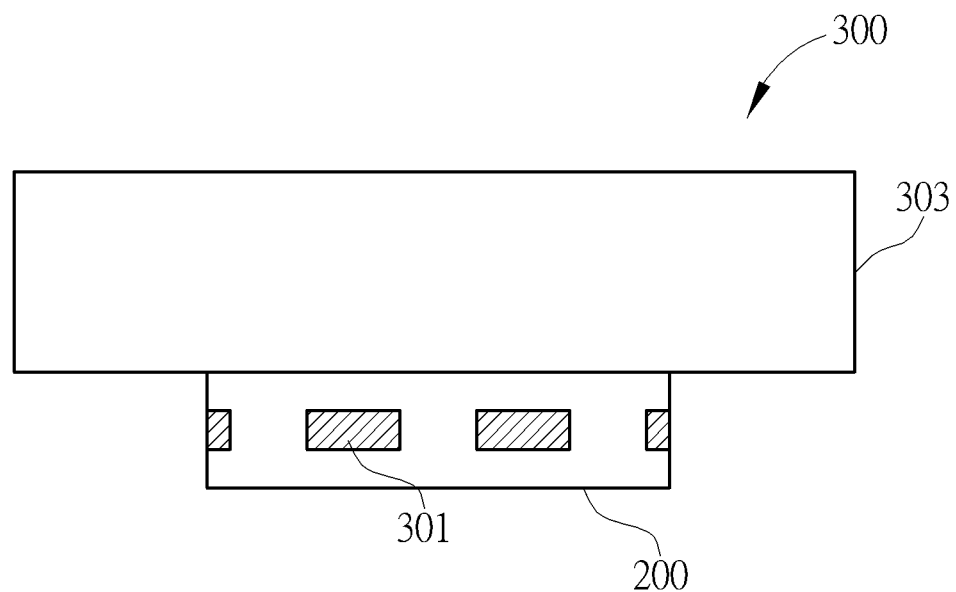

FIG. 2 and FIG. 3 are schematic diagrams illustrating structures of a smoke detector according to embodiments of the present invention. FIG. 3 illustrates an outer appearance of the smoke detector and FIG. 2 illustrates a structure of a smoke box in the smoke detector. As above-mentioned, the first light source LS_1, the second light source LS_2 and the light receiver 101 can locate in a smoke chamber 109 within the smoke box 200 as shown in FIG. 2. The smoke box 200 can comprise holes 301 connected to the smoke chamber 109, thereby the external air can flow into the smoke chamber 109. The smoke box 200 is part of the smoke detector 300, and the smoke detector 300 may further comprise a body 303 besides the smoke box 200. Additionally, the signal adjusting circuit 103, the driving and determining circuit 105, the alarm control circuit 107 and the alarm generating circuit 111 mentioned in FIG. 1 are provided in the body 303.

In following descriptions, the operations of performing the two stages smoke determination and adjusting the second original detecting signal IOS_2 will be explained in more details. Please note, in following examples, the first light beam L_1 emitted from the first light source LS_1 mainly contains infrared light, and the second light beam L_2 emitted from the second light source LS_2 mainly contains blue light. Additionally, an absorption spectrum of the light receiver 101 is greatest at infrared light, thus an energy conversion efficiency of the light receiver 101 for blue light is smaller than an energy conversion efficiency of the light receiver 101 for infrared light. However, the types of lights and the light receiver are not limited to these examples, any light beam and any light receiver can provide the function of the present invention should fall in the scope of the present invention.

Figure 4A:
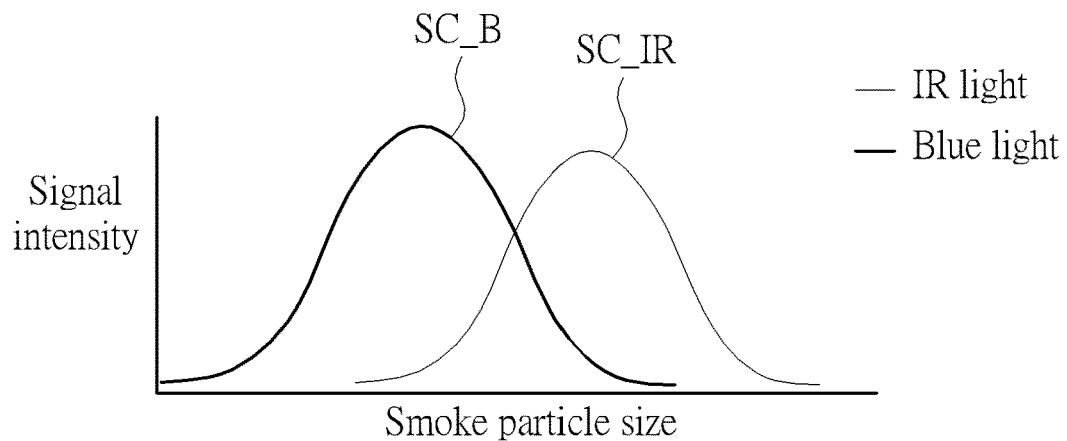
FIG. 4A, FIG. 4B and FIG. 4C are schematic diagrams illustrating operations of adjusting an original light detecting signal according to one embodiment of the present invention.
Figure 4B:
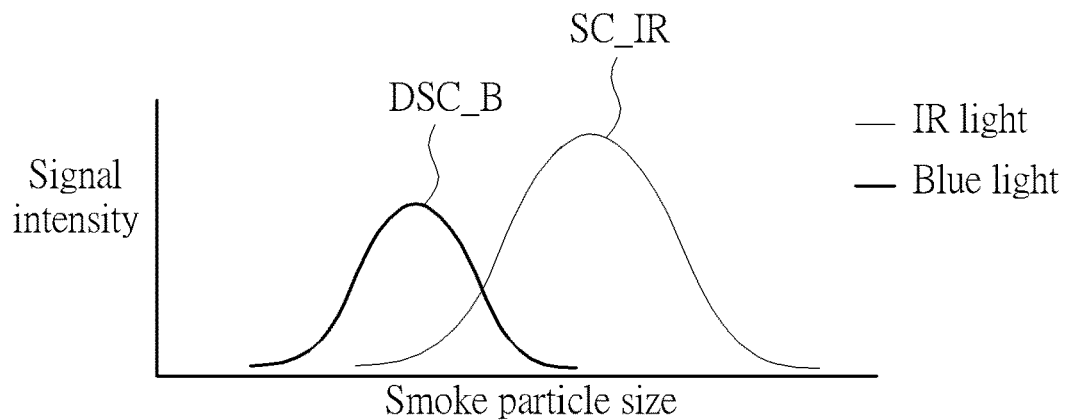
Figure 4C:
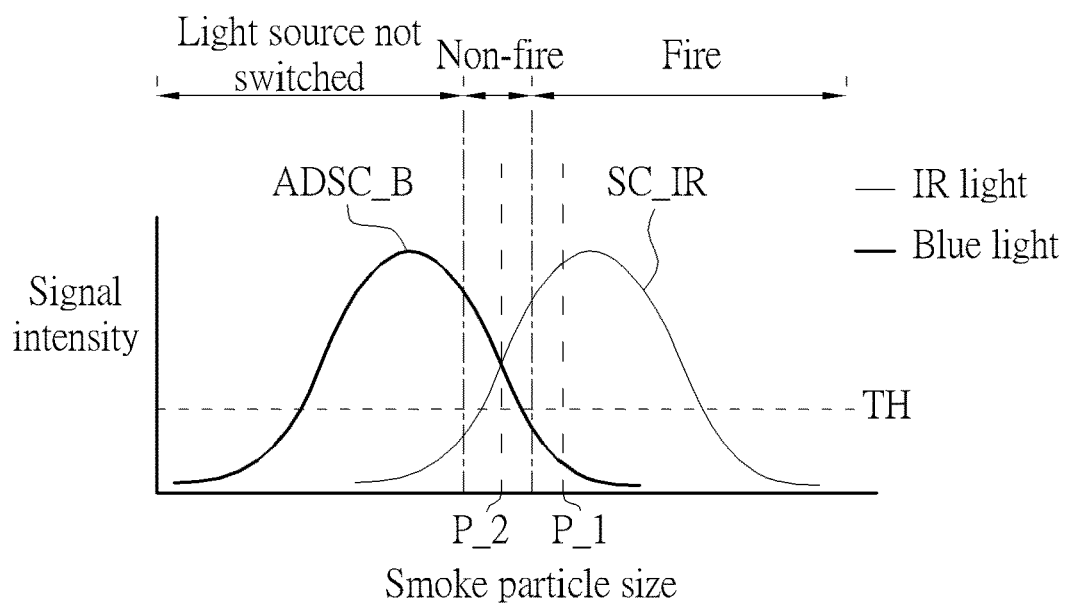

FIG. 4A, FIG. 4B and FIG. 4C are schematic diagrams illustrating operations of adjusting an original light detecting signal according to one embodiment of the present invention. The horizontal axes of FIG. 4A, FIG. 4B and FIG. 4C mean smoke particle sizes, and the vertical axes thereof mean signal intensities. The signal intensity and the scatter light intensity are related with sensitivities for different types of light to smoke particle sizes. The curve SC_B in FIG. 4A is a relation curve showing the relation between signal intensities and smoke particle sizes when a blue light receiver receives blue light, and the curve SC_IR in FIG. 4A is a curve showing the relation between signal intensities and smoke particle sizes when a IR (infrared) light receiver receives IR light. Based on FIG. 4A, blue light is more suitable for detecting small particles since it has shorter wavelengths, and IR light is more suitable for detecting large particles since it has longer wavelengths. Also, the smoke particles contained in fire smoke caused by a fire are always large particles, and the smoke particles contained in non-fire smoke are always small particles. The meanings of large particles and small particles can be defined corresponding to different requirements. For example, the particle having a diameter larger than a specific diameter is defined as a large particle, and the particle having a diameter smaller than the specific diameter is defined as a small particle.

In FIG. 4B, the curve DSC_B is a curve showing the relation between signal intensities and smoke particle sizes when an IR light receiver receives blue light. As above-mentioned, since the light receiver 101 is an IR receiver, the energy conversion efficiency thereof for blue light is smaller than the energy conversion efficiency thereof for IR light. Accordingly, the signal intensity decreases in such case even if the particle sizes are the same, and a range of detectable particle sizes is smaller than a range of detectable particle sizes in FIG. 4A. Therefore, in FIG. 4C, the second original light detecting signal IOS_2 is amplified by the signal adjusting circuit 103, to decrease a difference between signal conditions of light detecting signals received by the driving and determining circuit 105. In one embodiment, the second original light detecting signal IOS_2 is amplified to a second light detecting signal OS_2, thereby a difference between a maximum signal intensity of the second light detecting signal OS_2 and a maximum signal intensity of the first original light detecting signal IOS_1 can be reduced to fall in a predetermined range (in this embodiment, the maximum signal intensities are the same). Thus the curve showing relations between blue light signal intensities and smoke particle sizes is changed to the relation curve ADSC_B shown in FIG. 4C. In such case, the smoke detector 100 first uses the first light beam L_1 which mainly contains IR light to detect smoke. If a signal intensity of the first original light detecting signal IOS_1 is larger than a first signal threshold value (e.g. TH in 4C), it means smoke exists, but cannot determine whether the smoke particle sizes belong to a fire or not. In such case, the smoke detector 100 switches to use the second light beam L_2, which mainly contains blue light to detect the smoke. If a signal intensity of the second light detecting signal OS_2 is smaller than the second signal threshold value (e.g. TH in FIG. 4C, but not limited), the smoke is determined to be caused by a fire. For example, if the particle size is P_1 which indicates a fire, the signal intensity of the first original light detecting signal IOS_1 is larger than TH, but the signal intensity of the second light detecting signal OS_2 is smaller than TH. On the opposite, if the particle size is P_2 which indicates non fire, the signal intensity of the first original light detecting signal IOS_1 is larger than TH, and the signal intensity of the second light detecting signal OS_2 is also larger than TH. The "light source not switched" in FIG. 4C means the signal intensity of the first original light detecting signal IOS_1 is not larger than TH, thus the first light source LS_1 is continuously used for detecting smoke rather than switched to the second light source LS_2.

Figure 5:
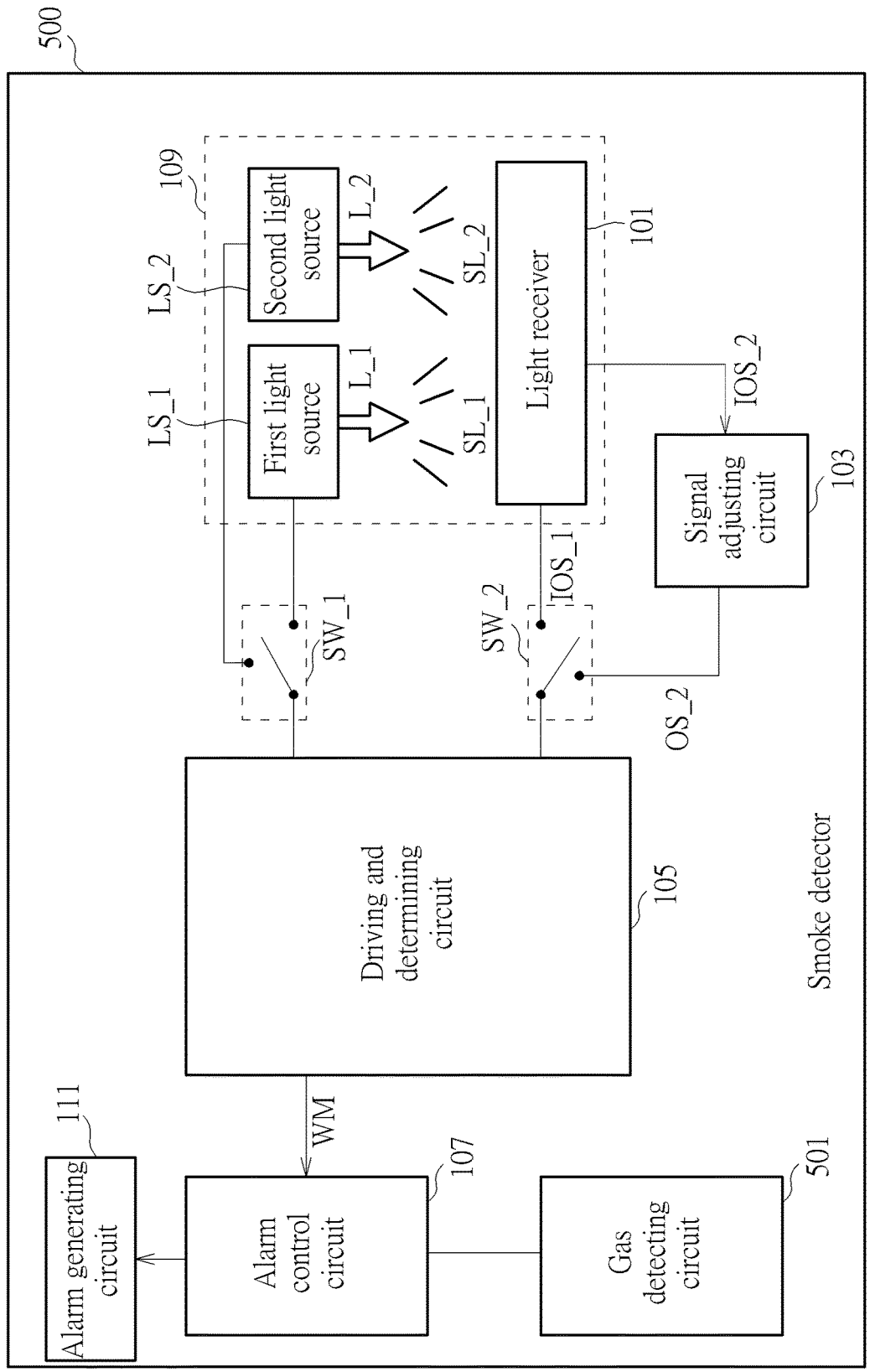
FIG. 5 is a circuit block diagram illustrating a smoke detector according to another embodiment of the present invention.

Besides the above-mentioned two stages smoke determining method, the smoke detector provided by the present invention can also use other mechanisms to determine whether a fire breaks out or not. FIG. 5 is a circuit block diagram illustrating a smoke detector according to another embodiment of the present invention. As illustrated in FIG. 5, the smoke detector 500 further comprises a gas detecting circuit 501 besides the components illustrated in FIG. 1, which can detect a concentration of specific gas. The specific gas can be gas which is always generated in a fire, such as carbon monoxide, cyanide, or haloalkane. In such embodiment, the alarm control circuit 107 controls the gas detecting circuit 501 to detect a concentration of specific gas rather than directly control the alarm generating circuit 111 to generate alarms while receiving the warning message WM. After that, if the concentration is larger than a concentration threshold value, the alarm control circuit 107 controls the alarm generating circuit 111 to generate alarms.

Figure 6:
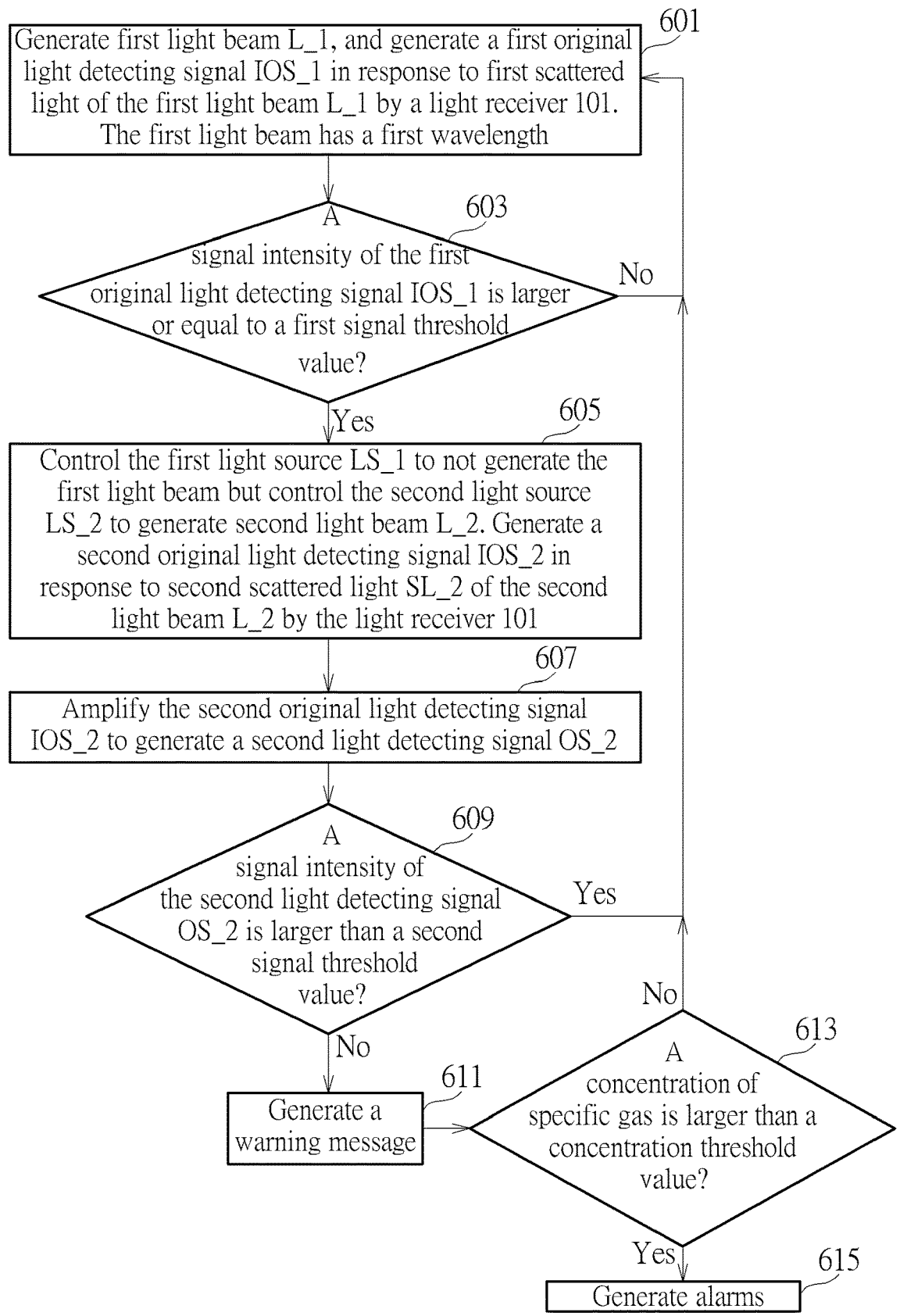
FIG. 6 is a flow chart illustrating a smoke detecting method according to one embodiment of the present invention.

In view of above-mentioned embodiments, a smoke detecting method can be acquired, which comprises following steps illustrated in FIG. 6:

Step 601

Generate first light beam L_1, and generate a first original light detecting signal IOS_1 in response to first scattered light of the first light beam L_1 by a light receiver 101. The first light beam has a first wavelength.

Step 603

Determine if a signal intensity of the first original light detecting signal IOS_1 is larger than or equal to a first signal threshold value. If yes, go to step 605, if not, go to step 601.

Step 605

Control the first light source LS_1 to not generate the first light beam but control the second light source LS_2 to generate second light beam L_2. Generate a second original light detecting signal IOS_2 in response to second scattered light SL_2 of the second light beam L_2 by the light receiver 101. The second light beam has a second wavelength.

Step 607

Amplify the second original light detecting signal IOS_2 to generate a second light detecting signal OS_2.

Step 609

Determine if a signal intensity of the second light detecting signal OS_2 is larger than a second signal threshold value. If yes, go to step 601, if not, go to step 611.

Step 611

Generate a warning message.

In one embodiment, the smoke detector 500 in FIG. 5 can enter the step 613 after the step 611. In the step 613, the gas detecting circuit 501 determines if a concentration of specific gas (e.g. carbon monoxide) is larger than a concentration threshold value. If the concentration is not larger than the concentration threshold value, the flow goes back to the step 601. If the concentration is larger than the concentration threshold value, the flow goes to the step 615, such that the alarm generating circuit 111 generates alarms. Besides, if the step 613 is omitted, the flow directly goes to the step 615.

In view of above-mentioned embodiments, two stages or more stages smoke detecting method can be applied to determine whether a fire breaks out or not, thus false alarms can be reduced. Additionally, the present invention can use a single light receiver to receive light of different spectrums, thus the circuit or device size and cost can be reduced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A smoke detector, comprising:
a first light source, configured to generate first light beam with a first wavelength;
a second light source, configured to generate second light beam with a second wavelength;
a light receiver, configured to generate a first original light detecting signal in response to first scattered light of the first light beam, and configured to generate a second original light detecting signal in response to second scattered light of the second light beam, wherein a first energy conversion efficiency of the light receiver at the first wavelength is different from a second energy conversion efficiency of the light receiver at the second wavelength;
a signal adjusting circuit, configured to amplify the second original light detecting signal to generate a second light detecting signal; and
a driving and determining circuit, coupled to the first light source, the second light source, the light receiver, and the signal adjusting circuit, configured to determine signal intensities of the first original light detecting signal and the second light detecting signal;
wherein if the driving and determining circuit determines a signal intensity of the first original light detecting signal is larger than or equal to a first signal threshold value, the driving and determining circuit controls the first light source to not generate the first light beam and the second light source to generate the second light beam, and then if the driving and determining circuit determines a signal intensity of the second light detecting signal is not larger than a second signal threshold value, the smoke detector generates a warning message.

2. The smoke detector of claim 1, further comprising:
an alarm control circuit, coupled to the driving and determining circuit; and
a gas detecting circuit, coupled to the alarm control circuit;
wherein if the alarm control circuit receives the warning message, the gas detecting circuit detects a concentration of specific gas, and if the concentration is larger than a concentration threshold value, the alarm control circuit controls an alarm generating circuit to generate an alarm.

3. The smoke detector of claim 2, wherein the specific gas is carbon monoxide.

4. The smoke detector of claim 1, wherein the first signal threshold value is equal to the second signal threshold value, and the first wavelength is larger than the second wavelength.

5. The smoke detector of claim 1, wherein the first light beam mainly contains infrared light, and the second light beam mainly contains blue light, and an absorption spectrum of the light receiver is greatest at infrared light.

6. A smoke detecting method, comprising:
generating first light beam by a first light source, and generating a first original light detecting signal in response to first scattered light of the first light beam by a light receiver, wherein the first light beam has a first wavelength;
controlling the first light source to stop generating the first light beam, generating second light beam by a second light source and generating a second original light detecting signal in response to second scattered light of the second light beam by the light receiver, if a signal intensity of the first light detecting signal is larger than or equal to a first signal threshold value, wherein the second light beam has a second wavelength;
amplifying the second original light detecting signal to generate a second light detecting signal; and
generating a warning message if a signal intensity of the second light detecting signal is not larger than a second signal threshold value.

7. The smoke detecting method of claim 6, further comprising:
detecting a concentration of specific gas if the warning message is generated, and generating an alarm if the concentration is larger than a concentration threshold value.

8. The smoke detecting method of claim 7, wherein the specific gas is carbon monoxide.

9. The smoke detecting method of claim 6, wherein the first signal threshold value is equal to the second signal threshold value, and the first wavelength is larger than the second wavelength.

* * * * *